United States Patent [19]

Pope

[11] Patent Number: 4,650,908

[45] Date of Patent: Mar. 17, 1987

[54] PRODUCTION OF ARYLACETALDEHYDES

[75] Inventor: Brian G. Pope, Baton Rouge, La.

[73] Assignee: The Dow Chemical Company, Midland, Mich.

[21] Appl. No.: 812,626

[22] Filed: Dec. 23, 1985

[51] Int. Cl.$^4$ .............................................. C07C 45/58
[52] U.S. Cl. .................................................... 568/427
[58] Field of Search ........................................ 568/427

[56] References Cited

U.S. PATENT DOCUMENTS

| | | |
|---|---|---|
| 2,628,255 | 2/1953 | Sexton et al. |
| 3,067,256 | 12/1962 | Fischer et al. ................ 568/427 X |
| 3,860,614 | 1/1975 | Watson ............................ 260/340.9 |
| 3,927,110 | 12/1975 | Watson ................................ 260/599 |
| 4,495,371 | 1/1985 | Neri et al. ......................... 568/427 |

*Primary Examiner*—Bernard Helfin

[57] ABSTRACT

This invention relates to the isomerization of monoarylethylene oxide in the presence of water over a silica gel catalyst. Reaction temperatures are relatively low, i.e., 160° C. to about 180° C.

7 Claims, No Drawings

PRODUCTION OF ARYLACETALDEHYDES

BACKGROUND OF THE INVENTION

This invention relates to the low temperature isomerization of monoaryl-ethylene oxides to form arylacetaldehydes. Such isomerization, to be economical, must provide high conversion of reactant to product, i.e., 90% and above, and exhibit good selectivity for the aldehyde product. Further, the isomerization should not require a long reaction time, a high temperature, i.e., above 180° C., or an expensive catalyst to achieve the desirable conversion and selectivity.

Therefore, it is an object of this invention to provide a highly economical process for the isomerization of a monoaryl-ethylene oxide, e.g., styrene oxide, to yield arylacetaldehyde, e.g., phenylacetaldehyde.

THE INVENTION

It has been discovered that high conversion and selectivity for the isomerization of monoaryl-ethylene oxides having the formula,

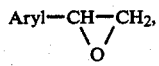

can be obtained by passing a vapor containing such monoaryl-oxide and from about 1 to about 10 weight % water, based upon the total weight of the monoaryl-oxide and water, into contact with a silica gel catalyst at a reaction temperature within the range of from about 160° C. to about 180° C.

The aryl constituent of the monoaryl-ethylene oxide reactant is defined as a monovalent aromatic hydrocarbon radical of the benzene series having its single valence on a carbon atom of the benzene nucleus. Examples of monoaryl-ethylene oxides are sytrene oxide, α-methyl styrene oxide, p-methyl-styrene oxide, m-chloro styrene oxide, etc. Styrene oxide is a preferred reactant as it yields the commercially valuable aldehyde, phenylacetaldehyde, which is used in the fragrance industry.

The silica gel catalyst used in the process of this invention may be any of those which are commercially available for use as catalysts. For example, BAKER ANALYZED SILICA GEL, manufactured by J. T. Baker Chemical Co., Phillipsburg, N.J., and BRIGHTSORB, manufactured by The PQ Corp., Valley Forge, Pa., are suitable. The ability of the process of this invention to use such an inexpensive catalyst constributes to its commercial acceptability.

It is an important feature of this invention that the monoaryl-ethylene oxide containing vapor contacted with the silica gel catalysts additionally include water vapor. It has been found that the conversion and selectivity percentages for the reaction are greatly enhanced when water is present. The water vapor may be present in an amount within the range of from about 1 to about 10 weight percent and is preferably present in an amount within the range of from about 2 to about 6 weight percent. These weight percents are based upon the total weight of monoaryl-ethylene oxide and water in the vapor. The use of water in an amount less than 1 weight percent, say 2 ppm, has not been found effective.

The reaction temperature for the instant process and thus the temperature of the silica gel catalyst is quite low, i.e., between 160° C. and 180° C., when compared to some of the other prior art processes which report preferred temperature ranges above 200° C. The silica gel catalyst may be kept at the reaction temperatures by heating it or by raising the temperature of the vapor to the required temperature prior to contacting same with the catalyst. In practice, the monoaryl-ethylene oxide is first provided as a liquid in a mixing pot and has added to it an amount of liquid water which is within the above-stated ranges. The resultant mix is agitated and heated to a temperature within the range of from about 100° to about 150° C. so that it evolves a vaporous monoaryl-ethylene oxide/water mix which, quantitatively, represents the original mix. It is preferred that the process of this invention be run as a continuous process, thus, as the vaporous mix is continuously removed from the mixing pot, make-up monoaryl-ethylene oxide and water are introduced thereto.

The monoaryl-ethylene oxide/water containing vapor from the mixing pot is introduced to a reaction vessel in which the silica gel is contained. To facilitate the transport of the vapor from the mixing pot to the reactor, it is preferred that an inert gas, e.g., $N_2$, Ar, be used to continuously sweep the mixing pot of its vapor. The resultant vapor mix, which now additionally contains the inert gas, will have a feed velocity to the reactor which is at least partly determined by the velocity of the inert gas entering the reaction pot. The feed velocity will determine, for any particular reactor design, the contact time between the resultant vapor and the silica gel catalysts. For good results, the process of the invention does not require long contact times but rather is very efficient using contact times as low as 1 second. Preferred contact times are within the range of from about 3 seconds to about 5 seconds.

Not only does the use of the inert gas provide for achievement of the foregoing contact times, it also acts as a diluent. It is desirable that an inert diluent be used so as to minimize the production of aldol dimers, which production would adversely affect selectivity. For example, when the inert gas is nitrogen at 150° C. and atmospheric pressure, the resultant vapor mix should have a monoaryl-ethylene oxide concentration of from about 5% to about 10% by weight. Lower concentrations, while yet further reducing dimer production, are not desirable as they lower the amount of aldehyde product produced per unit time.

Since the liquid mix in the mixing pot is being heated to continuously yield a vapor, the inert gas should be preferably introduced in a heated state to prevent cooling and condensation of the vapor. To achieve this end, the inert gas can be heated to a temperature within the range of from about 100° to about 150° C. before introduction to the mixing pot.

As mentioned previously, the liquid mix is agitated to promote heterogenity. One convenient method of agitation is to sparge the inert gas through the liquid mix. The inert gas thus used can be fed to the liquid mix at its bottom through a single port or through multiple ports as the need requires.

The reaction may be carried out at any convenient pressure. Atmospheric pressure is preferred from a process cost standpoint.

The method, as just described, is indicated for isomerizing any monoaryl-ethylene oxide having the aforementioned general formula to produce a corresponding arylacetaldehyde in good yield. For instance, it may be applied in isomerizing styrene oxide to obtain phenylacetaldehyde, in isomerizing a methyl-styrene oxide to produce a methylphenylacetaldehyde, in isomerizing a dimethyl-styrene oxide to obtain a dimethylphenylacetaldehyde, or in isomerizing an ethyl-styrene oxide to form an ethylphenylacetaldehyde, etc.

The following examples are provided to illustrate the practice of this invention and are not to be construed as limiting in scope.

EXAMPLE I

A 500 cc pot is charged with 20 gms of styrene oxide and 0.4 gm water. The pot is heated to 150° C. to increase the vapor pressure of the styrene oxide. A stream of nitrogen at 1000 cc/min is bubbled through the hot styrene oxide/water system. It is approximated that 1 gm of styrene oxide is picked up every 15,000 cc of nitrogen. This hot gas mixture is passed into a 50 cc bed of silica gel heated to 175° C. The hot vapor passes through the bed and is then passed to a heat exchanger which condenses the liquid product but not the carrier gas. Residence time in the catalyst bed is calculated to be within 3–5 seconds. The amount of silica gel packed into the 50 cc bed is approximately 100 gms. Gel Permeation Chromotography (GPC) analysis of the resultant product showed a 97% conversion and a 96% selectivity. The yield, therefore, was 93%.

EXAMPLE II

The procedure of Example I was followed except that 25 grams of styrene oxide and 0.45 grams of water were used. GPC analysis of the resultant product showed a 100% conversion and a 94% selectivity. The yield was 94%.

EXAMPLE III

The procedure of Example I was followed except that no water was used. GPC analysis of the product showed a 51% conversion and a 98% selectivity. Thus, the yield was 50%.

As can be seen from a comparison between Examples I and II, which illustrates processes of this invention, and Example III, which illustrates a process not of this invention, that the presence of water in the reaction system is of substantial benefit to the yield of the isomerization of styrene oxide.

I claim:

1. A process for the isomerization of monoaryl-ethylene oxide to yield an arylacetaldehyde, which process comprises: contacting, at a temperature within the range of from about 160° C. to about 180° C., a vapor containing said monoaryl-ethylene oxide and water with a silica gel catalyst, said water being present in an amount within the range of from about 1 to about 10 weight percent, based upon the total weight of said monoaryl-ethylene oxide and said water.

2. The process of claim 1 wherein said monoaryl-ethylene oxide is styrene oxide and said arylacetaldehyde is phenylacetaldehyde.

3. The process of claim 1 wherein said vapor contains from about 2 to about 6 weight percent water.

4. The process of claim 2 wherein said vapor contains from about 2 to about 6 weight percent water.

5. The process of claim 1 wherein said vapor additionally contains a nitrogen diluent.

6. The process of claim 5 wherein said vapor contains from about 5 weight percent to about 10 weight percent monoaryl-ethylene oxide.

7. The process of claim 1 wherein said vapor consists essentially of said monoaryl-ethylene oxide, said water and nitrogen.

* * * * *